United States Patent [19]
Grimm

[11] Patent Number: 5,522,797
[45] Date of Patent: Jun. 4, 1996

[54] SLIDE ACTION VETERINARY IMPLANTER

[75] Inventor: C. Louis Grimm, Shawnee, Kans.

[73] Assignee: Ivy Laboratories, Inc., Overland Park, Kans.

[21] Appl. No.: 367,731

[22] Filed: Jan. 3, 1995

[51] Int. Cl.[6] ..................................................... A61M 5/18
[52] U.S. Cl. ............................................. 604/61; 604/63
[58] Field of Search ................................ 604/61, 62, 57, 604/59, 63, 64

[56] References Cited

U.S. PATENT DOCUMENTS

| | | |
|---|---|---|
| 842,631 | 1/1907 | Deperdussin . |
| 1,109,072 | 9/1914 | Kozmousky . |
| 1,248,613 | 12/1917 | Chapman . |
| 1,347,622 | 7/1920 | Deininger . |
| 2,502,909 | 4/1950 | Wick et al. . |
| 2,850,013 | 9/1958 | Cordis . |
| 2,883,984 | 4/1959 | Candido, Jr. et al. . |
| 3,520,299 | 7/1970 | Lott et al. . |
| 3,538,916 | 11/1970 | Wiles et al. . |
| 3,669,104 | 6/1972 | Wyatt et al. . |
| 3,774,607 | 11/1973 | Schmitz . |
| 4,154,239 | 5/1979 | Turley . |
| 4,223,674 | 9/1980 | Fluent et al. . |
| 4,400,170 | 8/1983 | McNaughton et al. . |
| 4,447,223 | 5/1984 | Kaye et al. . |
| 4,518,384 | 5/1985 | Tarello et al. . |
| 4,576,591 | 3/1986 | Kaye et al. . |
| 4,637,816 | 1/1987 | Mann . |
| 4,659,326 | 4/1987 | Johnson et al. . |
| 4,673,387 | 6/1987 | Phillips et al. . |
| 4,687,465 | 8/1987 | Prindle et al. ............................ 604/61 |
| 4,762,515 | 8/1988 | Grimm . |
| 4,784,640 | 11/1988 | Johnson et al. . |
| 4,787,384 | 11/1988 | Campbell et al. . |
| 4,799,921 | 1/1989 | Johnson et al. . |
| 4,976,686 | 12/1990 | Ball et al. ................................ 604/61 |
| 5,135,493 | 8/1992 | Peschke . |
| 5,147,295 | 9/1992 | Stewart .................................... 604/61 |

*Primary Examiner*—John D. Yasko
*Attorney, Agent, or Firm*—Litman, McMahon and Brown

[57] ABSTRACT

A slide action veterinary implanter apparatus includes a tubular housing having a hand grip extending therefrom with a trigger assembly pivotally mounted in the hand grip. A slide member is slidably mounted on the housing and retracts an impeller member to a retracted position, extends the trigger to an armed position, and advances a pellet magazine, extending through the hand grip, by reciprocation of the slide member. Additionally, a latch mechanism engaged with the slide mechanism, the trigger, and the impeller causes an impeller extending force to be stored and retained in an impeller extender spring as the slide member is reciprocated. Pivoting the trigger into the hand grip toward a release position releases the latch mechanism, whereby the extender spring force resiliently urges the impeller through a pellet magazine chamber driving a stack of pellets therefrom and through a needle mounted on the front end of the implanter housing. An impeller bias spring maintains a outward resilient force on the impeller whereby the pellets are completely ejected from the needle as the needle is withdrawn from the ear of an animal receiving the implant.

27 Claims, 6 Drawing Sheets

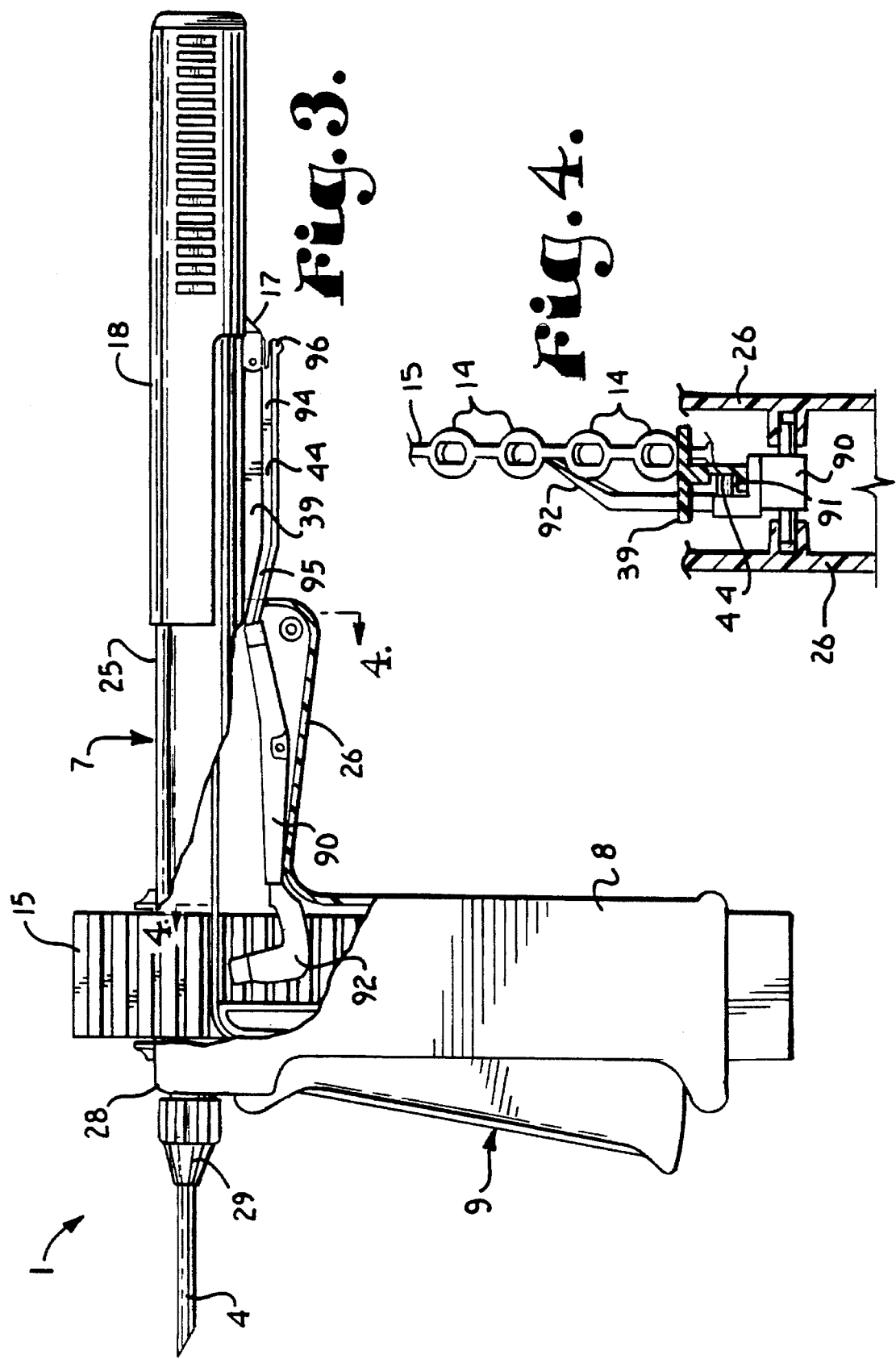

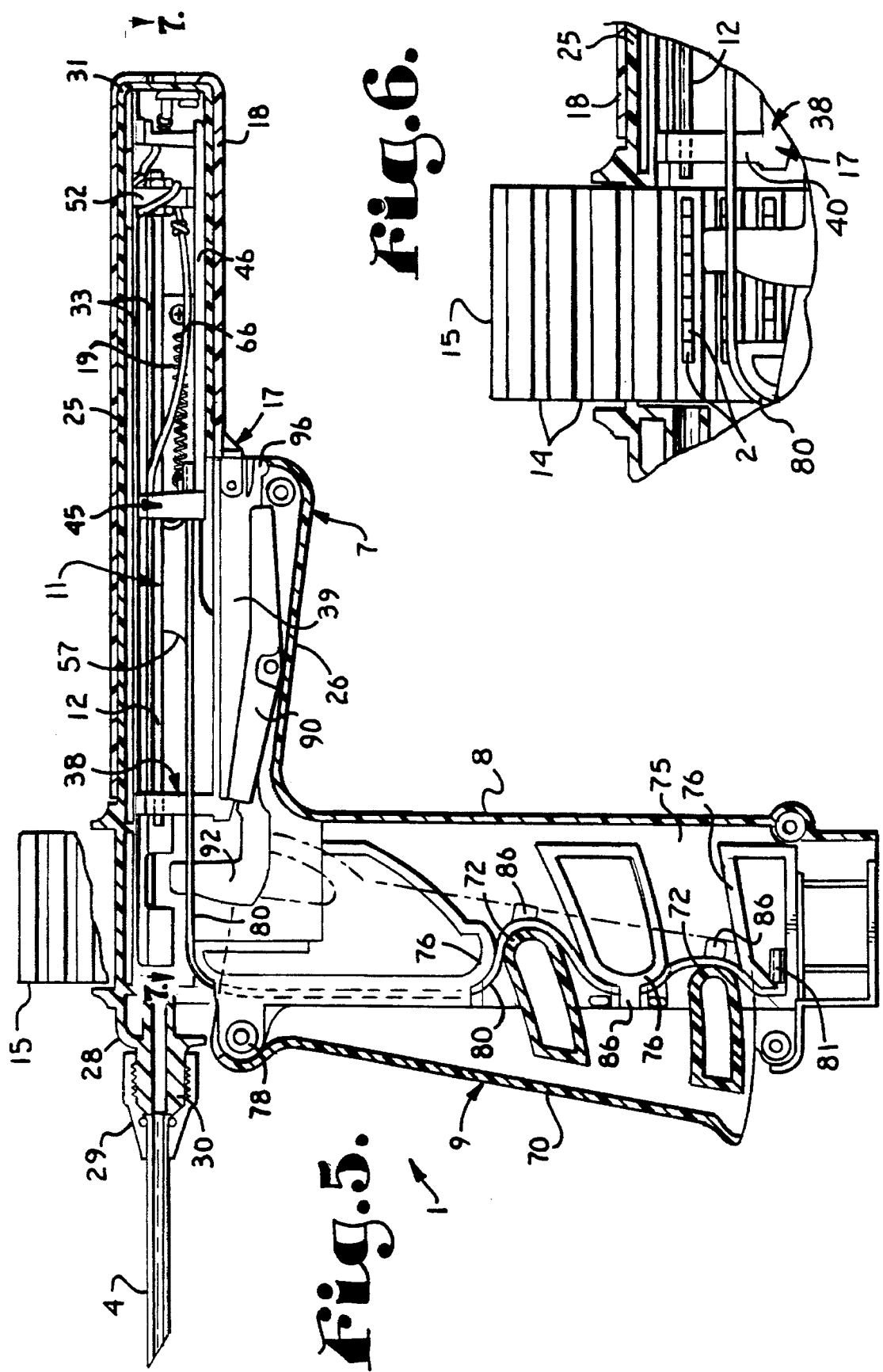

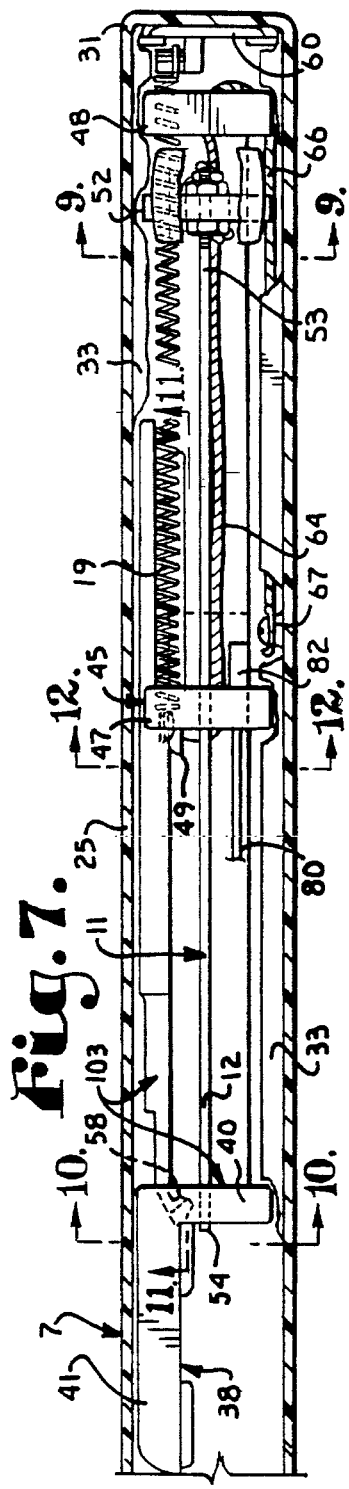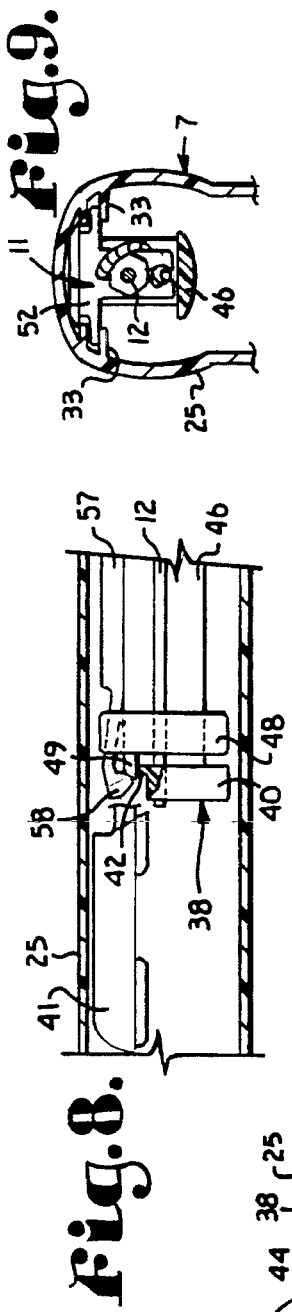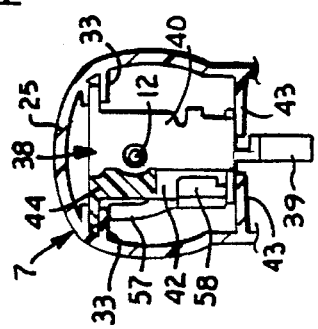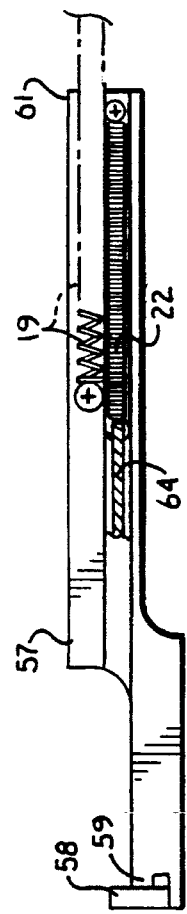

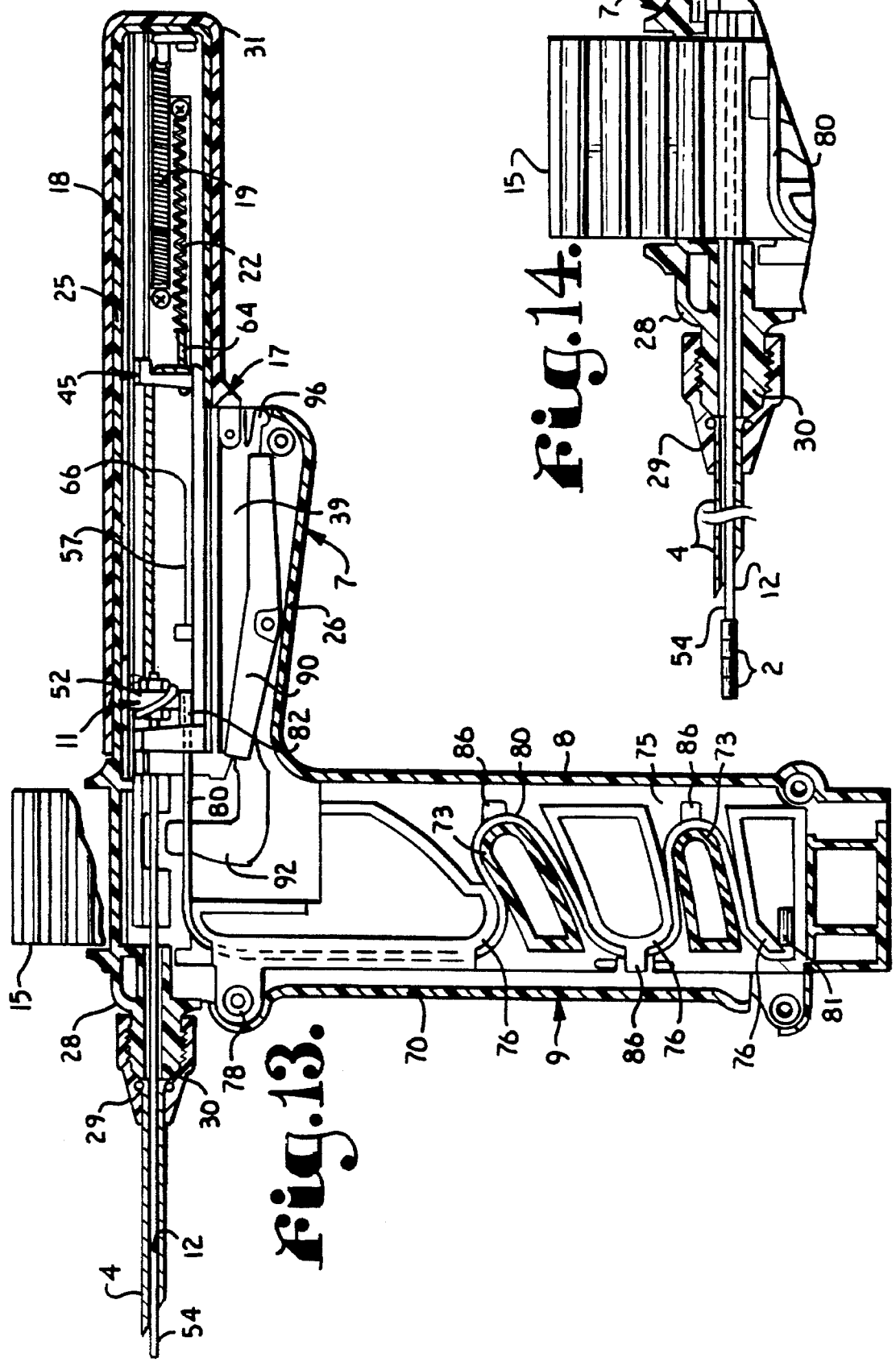

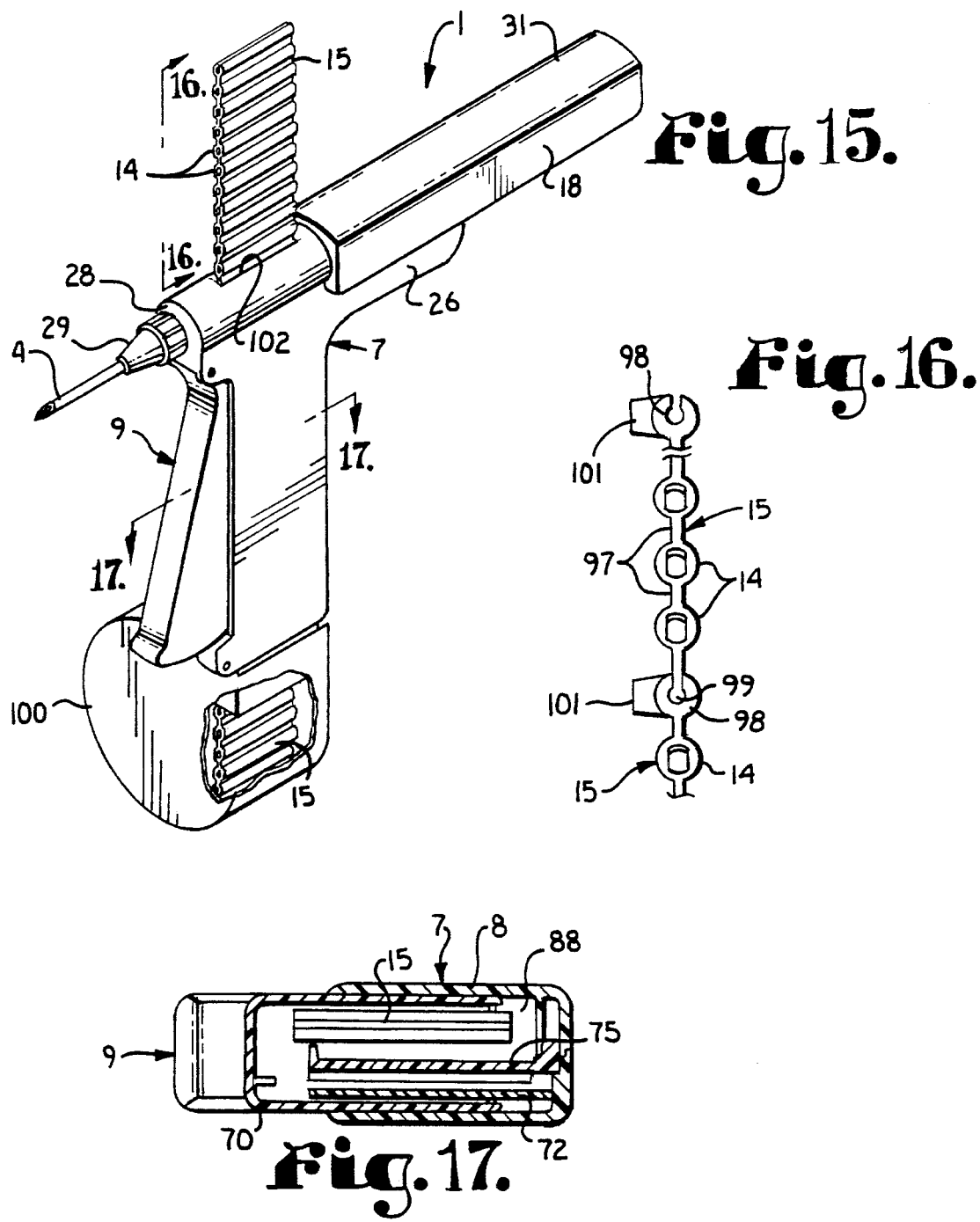

5,522,797

SLIDE ACTION VETERINARY IMPLANTER

BACKGROUND OF THE INVENTION

Currently, growth stimulants are used to enhance the body weight of animals which are raised for slaughtering, such as cattle, swine, turkeys, chickens, and the like. In the case of cattle and swine, approved growth hormones are administered as solid pellets which are injected into the ears of such animals. The ears are commonly discarded in slaughtering, such that no unabsorbed residues of such pellets will end up in food products intended for humans or domestic animals. The pellets are formulated for timed release and absorption of the active ingredients over an extended period of time.

The pellets are normally implanted while an animal is confined in a chute. An ear is grasped in one hand, and an implanter device having a large hypodermic needle is used to puncture the hide to enable a pellet dose to be injected between the hide and the next layer of tissue in the ear. The implanting must be done carefully to insure that the pellets are properly placed and that no pellet remains in the puncture in the hide, which could result in an infection. At the same time, the procedure must be carried out quickly since the animals are not entirely cooperative and may shake their heads to free the held ear. Further complicating the matter is that other procedures may be occurring at the same time as the implanting operation while the animal is confined, such as ear tagging, branding, veterinary inspections or procedures, or the like, which may further excite the animal.

The great majority of implanter devices employ manual gripping force on a trigger and a hand grip of such a device to propel an impeller through a pellet holding device or magazine to drive the pellets through the needle and into the space formed by the needle as the needle is withdrawn from the ear. Most implanters have a spring arrangement whereby an impeller return force is stored in the spring as the impeller is driven forward by operation of the trigger to return the impeller to its retracted position when the trigger is released. With such an arrangement, pellet implanting is complicated by the need to coordinate withdrawal of the needle as the pellets exit the needle. Such complexity of motion coupled with fatigue from using grip strength to eject the pellets can result in mistakes, such as lodging a pellet in the hide puncture or some of the pellets being ejected onto the ground.

U.S. Pat. No. 4,672,515 discloses an implanter which latches the trigger in the extreme extended position of the implanter and which provides a spring bias to the impeller in its extended position which causes the pellets to be automatically ejected as the needle is withdrawn from the ear of the animal. A release lever is operated to release the trigger latch after the needle is withdrawn to allow the impeller to return to its retracted position. Such an arrangement greatly increases the potential accuracy of implanting. However, fatigue can still be a factor since the grip strength of the person performing the implanting is used to propel the impeller against the force of the return spring arrangement.

A number of implanter devices use multiple pellet dose magazines to hold a plurality of pellet doses. Each pellet dose usually consists of a plurality of small pellets of a measured drug dosage which are positioned in an in-line orientation within a cylindrical chamber of the magazine. The magazine is a strip having a plurality of such chambers arranged in parallel relation, such as by being connected by webs between the chambers. Although some implanters are known to have magazines which advance to the next magazine chamber each time an implant operation occurs, most implanters require manual advancing of their magazines. Such manual advancing of the pellet magazine requires that the person performing the implanting operation remember to advance the magazine after each operation. If the magazine is not advanced, no pellets will be injected.

SUMMARY OF THE INVENTION

The present invention provides an improved implanter apparatus which overcomes many of the problems of implanters previously employed in implanting solid form drugs or medicaments into animals. The implanter of the present invention employs a slide action mechanism to retract an impeller, store an impeller driving force in a spring in cooperation with a latch mechanism, reset the trigger, and advance a pellet magazine, all by a single reciprocation of the slide mechanism. Pivoting the trigger into the hand grip draws the impeller forward to a point at which the latch mechanism releases the spring which resiliently drives the impeller through the aligned magazine chamber and propels the pellets into the needle. The implanter, additionally, provides a spring bias to the impeller in its extreme extended position which causes the pellets to be automatically ejected from the needle as the needle is withdrawn from the animal's ear. An implanting procedure using the implanter of the present invention can be carried positively and accurately with relatively little fatigue in the arm muscles of the person administering the implanted drugs.

The implanter apparatus of the present invention includes housing with a tubular main housing section having a grip housing section depending therefrom. An elongated release shuttle with upstanding front and rear walls is slidably mounted within the main housing and has a latch release cam extending from the front end. An impeller carrier is slidably mounted between the front and rear walls of the shuttle and has an elongated impeller extending forwardly therefrom through the front wall of the shuttle and in alignment with a hypodermic needle mounted on and extending from the front end of the main housing. An impeller retractor cable or string is connected between the housing and the impeller carrier and passes about the rear wall of the shuttle. The latch mechanism includes a spring carrier having a latch pawl at a front end and slidably mounted in the main housing. An impeller drive or main spring is connected between the spring carrier and the rear end of the main housing. An impeller extender cable or string is connected to the impeller carrier and by an impeller bias spring to the spring carrier. The extender cable passes about the front wall of the shuttle.

A tubular slide grip telescopes onto the rear end of the main housing for reciprocating movement thereon and is connected to an internal slide bracket which is slidably mounted within the main housing. The slide bracket has an upstanding bumper wall positioned forward of the front wall of the shuttle and having the impeller extending therethrough. A latch shoulder is formed at a position on the bumper to be engaged by the latch pawl, as will be described.

A trigger assembly is pivotally mounted within the grip section of the housing and is of a hollow configuration. A trigger cable is engaged between portions of the trigger assembly and the shuttle. In a preferred embodiment of the present invention, the trigger assembly includes a fixed trigger finger plate mounted within the grip housing and a movable trigger plate mounted in a trigger shell. The trigger finger plates have corresponding trigger cable fingers which cooperatively engage the trigger cable and force it into a deepening sinuous or S-shaped pattern as the trigger shell is pivoted into the grip housing. Pivoting the trigger shell between an outward armed position and an inward release position, thus, takes up the length of the trigger cable and draws the end which is connected to the shuttle toward the trigger assembly.

The implanter of the present invention employs a pellet magazine which is formed by a strip of parallel pellet chambers connected by web sections between the chambers. The ends of the magazine are cooperatively formed so that the top end of one magazine can removably attach to the bottom end of another. The magazine extends through hollow portions formed in the grip housing and the trigger assembly toward the top side of the implanter and out an upper magazine port in the top of the main housing. The magazine is automatically advanced one chamber for each reciprocation of the slide grip. A magazine feed rocker is pivotally mounted within the housing, has a magazine feed pawl at a front end, and a cam follower at a rear end. The slide bracket has a linear cam track formed therein which the cam follower rides in. Reciprocation of the slide grip backward then forward causes the feed pawl to respectively slip past a magazine chamber then engage the chamber and advance the magazine upward to align the next chamber with the needle and the pawl. The implanter may also include a magazine drum which is received on the lower end of the grip housing and which stores a plurality of interconnected magazine strips which are rolled up within the drum.

Pulling the slide grip back engages the slide bracket bumper with the front wall of the shuttle, urging it backward. The retractor cable passing about the rear wall of the shuttle draws the impeller carrier backward at double the rate of the shuttle. As the slide bracket is drawn backward, the latch shoulder slips past the latch pawl. At the end of the rearward stroke of the slide grip, the shuttle is retracted fully backward along with the impeller carrier, which retracts the front or distal end of the impeller clear of the pellet magazine. The trigger shell is pivoted outward to an armed position by rearward movement of the shuttle, to which the trigger shell is connected by the trigger cable. A forward stroke of the slide grip moves the slide bracket forward whereby the latch shoulder engages the latch pawl, thereby moving the spring carrier forward and tensioning the main spring. As described above, reciprocation of the slide grip also advances the pellet magazine.

As the trigger shell is pivoted into the grip housing, the trigger cable pulls the shuttle and impeller forward, thereby extending the impeller end through the aligned magazine chamber whereby the pellet dose or stack is urged toward the needle. As the entire pellet stack enters the needle, the release cam on the shuttle engages the latch pawl, releasing it from the latch shoulder, and allows the spring carrier to snap backward. Backward movement of the spring carrier with the shuttle in a forward position is transferred to the impeller carrier through the impeller extender cable and bias spring, resiliently urging the impeller toward its fully extended position and engaging the impeller bias spring. The bias spring, to some extent, cushions the force of the impeller on the pellet stack, once the spring carrier is released from its latched position. The main function of the bias spring is to apply a resilient force to the impeller to cause positive ejection of the pellet stack as the needle is withdrawn from ear of the animal receiving the implant.

OBJECTS AND ADVANTAGES OF THE INVENTION

The principal objects of the present invention are: to provide an improved device for implanting solid forms of drugs, particularly into animals; to provide such a device of the type including a large hypodermic needle which is used to puncture the skin or hide of an animal and through which a dose of pellets is moved by an elongated impeller member; to provide such a device which enhances the accuracy and efficiency of an implanting operation and which reduces arm and hand fatigue in the person performing the implanting operation; to provide such a device in which the impeller is retracted and a trigger is armed by reciprocation of a slide member; to provide such a device in which pivoting the trigger toward a release position causes the impeller to be urged forward, eventually releasing a spring which drives a stack of pellets from a magazine chamber and through the needle; to provide such a device which provides an outward spring bias to the impeller to cause to pellets to be automatically ejected from the needle as the needle is withdrawn from the skin or hide of the animal receiving the implant; to provide such a device which employs an arrangement of cables to transfer operational movements within the implanter device, including retraction of the impeller in response to backward movement of the slide member and extension of the impeller in response to pivoting the trigger; to provide such a device including a pellet magazine including an elongated strip of parallel oriented pellet chambers which extends through a grip portion of the implanter housing; to provide such a device which automatically advances the magazine to align a new pellet chamber with the needle and impeller in response to reciprocation of the slide member; and to provide such a slide action veterinary implanter device which is economical to manufacture, which is positive and efficient in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a left side elevational view of the implanter apparatus with a slide member shown in a fully extended position.

FIG. 4 is a greatly enlarged transverse sectional view taken on line 4—4 of FIG. 3 and illustrates details of a magazine feed mechanism of the implanter apparatus.

FIG. 5 is a longitudinal sectional view of the implanter apparatus illustrating components of the apparatus in an "armed" state and ready for an implanting operation.

FIG. 6 is a somewhat enlarged fragmentary view similar to FIG. 5 and illustrates details of a pellet magazine strip and a magazine feed pawl.

FIG. 7 is an enlarged fragmentary longitudinal sectional view taken in plan on line 7—7 of FIG. 5 and illustrates details of internal components of the implanter apparatus in a nearly armed state.

FIG. 8 is a fragmentary view similar to FIG. 7 and illustrates details of a latch pawl of a spring carrier member and a latch shoulder of an internal slide bracket of the slide mechanism of the implanter apparatus.

FIG. 9 is a fragmentary transverse sectional view taken on line 9—9 of FIG. 7 and illustrates internal details just forward of an impeller carrier of the implanter apparatus.

FIG. 10 is a fragmentary transverse sectional view taken on line 10—10 and illustrates internal details just forward of a front wall of a release shuttle of the implanter apparatus.

FIG. 11 is a side elevational view of a spring carrier member of the implanter apparatus.

FIG. 12 is a fragmentary transverse sectional view taken on line 12—12 and illustrates internal details forward of a bumper wall of the internal slide bracket of the slide mechanism of the implanter apparatus.

FIG. 13 is a longitudinal sectional view of the implanter apparatus illustrating components of the apparatus in a released state after completion of an implanting operation.

FIG. 14 is an enlarged fragmentary view detailed view similar to FIG. 13 and illustrates spatial relationships of the impeller member, a pellet magazine chamber, and the hypodermic needle of the implanter apparatus.

FIG. 15 is a perspective view of the implanter apparatus illustrating a magazine drum for storing a plurality of pellet magazine strips connected in end to end relation.

FIG. 16 is a greatly enlarged front elevational view of a pellet magazine for use with the implanter apparatus, taken on line 16—16, and illustrates the manner of connecting multiple magazine strips in end to end relationship.

FIG. 17 is an enlarged transverse sectional view of the grip section of the housing of the implanter apparatus and illustrates details thereof along with details of a trigger assembly of the apparatus.

DETAILED DESCRIPTION OF THE INVENTION

Figure 1:
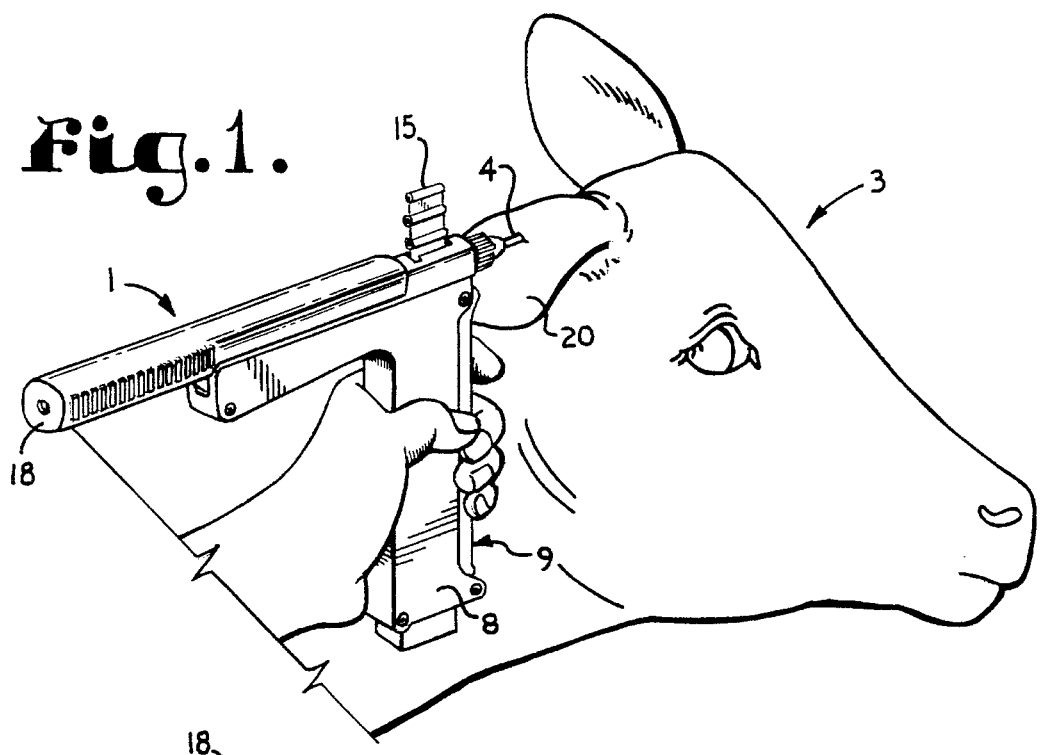
FIG. 1 is a perspective view of a slide action veterinary implanter apparatus which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a slide action veterinary implanter apparatus which embodies the present invention. The apparatus 1 is used to implant solid form drugs, such as pellets 2, FIG. 6, into an animal 3 through a hypodermic needle 4.

The implanter apparatus 1 generally includes a housing 7 having a grip portion 8 with a trigger assembly 9 pivotally mounted therein. An impeller assembly 11 (FIG. 5), including an impeller member 12, is slidably mounted within the housing 7 in alignment with the needle 4 and a chamber 14 of a pellet magazine 15. A slide mechanism 17, including an external slide member 18, is mounted on the housing 7 and is internally engaged with the impeller assembly 11, the trigger assembly 9, and the pellet magazine 15 to retract the impeller assembly 11 within the housing 7, pivot the trigger assembly 9 to an extended and armed position, store an impeller extension force in an impeller extender spring 19 (FIG. 7), and advance the pellet magazine 15 by reciprocation of the slide member 18. The needle 4 is used to puncture through the skin or hide of a part of the animal 3, such as an ear 20, and the trigger assembly 9 is pivoted into the grip portion 8 of the housing, causing impeller member 12 to be urged by the extender spring 19 through the magazine chamber 14, thereby forcing a stack of pellets 2 through the needle 4. An impeller bias spring 22 is engaged with the impeller 12 in such a manner that the impeller 12 ejects the pellets 2 from the needle 4 as the needle 4 is withdrawn from the ear 20 of the animal 3.

Figure 2:
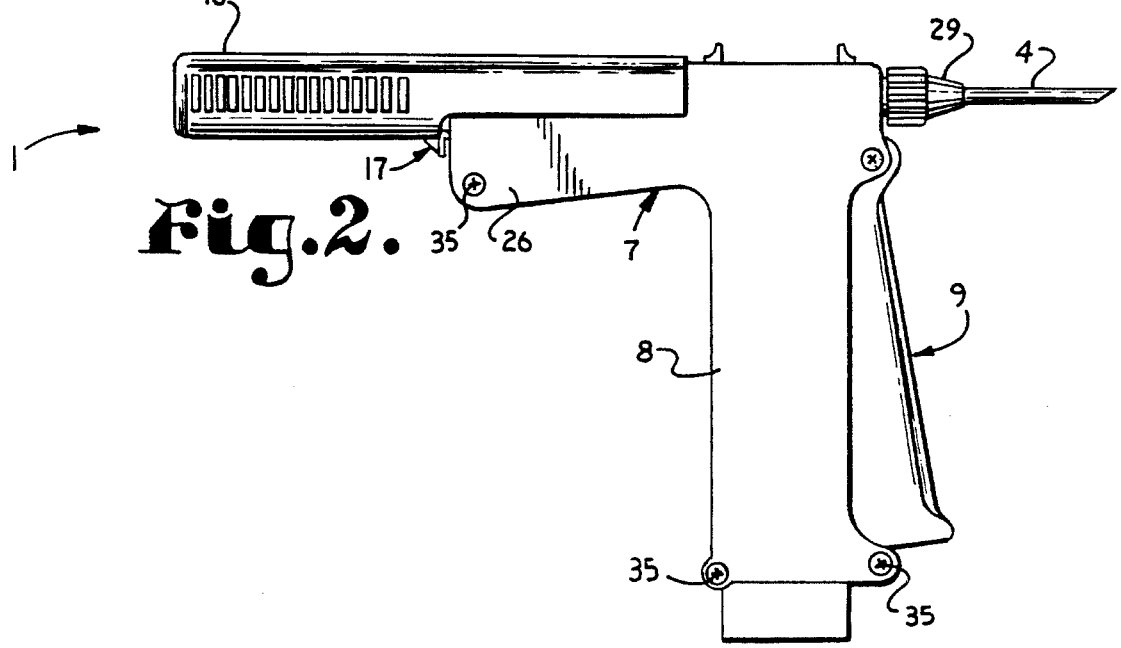
FIG. 2 is a right side elevational view of the implanter apparatus of the present invention.

Referring to FIGS. 4 and 5, the housing 7 includes the grip portion or grip housing 8, a tubular slide housing portion 25, and a rocker housing portion 26. The grip housing 8 extends at approximately a right angle to the slide housing 25. At a front end of the housing 7, a threaded nut 29 secures the needle 4 to the housing 7 by way of a threaded extension 29 of the housing 7 which has complementary threads. The slide member or slide grip 18 is tubular and is telescoped over a rear end 31 of the slide housing portion 25 and is slidable thereon. Parallel guide tracks 33 are formed on internal surfaces of the slide housing 25 in transversely spaced relation near an upper side of the slide housing 25. The tracks 33 (FIGS. 7, 9, 10, and 12) extend along a substantial portion of the length of the slide housing 25. The housing 7, the trigger assembly 9, and the majority of the components of the implanter 1 are formed of plastics, as by molding. The housing 7 is formed in lateral halves which are joined, as by fasteners 35, such as screws (FIG. 2).

Referring particularly to FIGS. 7–12, the slide mechanism 17 includes an internal slide bracket 38 including an elongated connector link 39, a bumper wall 40 upstanding from the connector link 39, and a magazine grip 41 extending forwardly from the bumper wall 40. A latch shoulder 42 is formed on a front edge of the bumper wall 40. The slide bracket 38 is slidably mounted in the tracks 33 within the slide housing 25 and rides on a pair of ledges 43 extending inwardly from the sides of the slide housing 25 (FIG. 10). A rear end of the connector link 38 is connected to the slide grip 18 so that the slide bracket 38 is moved whenever the slide grip 18 is moved. The connector link 39 has a linear cam track 44 formed therein (FIG. 3).

An elongated release shuttle 45 is slidably mounted in the tracks 33 rearward of the bumper wall 40. The shuttle 45 includes a floor member 46 with a front shuttle wall 47 and a rear shuttle wall 48 upstanding from opposite ends thereof. The front wall 47 has a latch release cam 49 extending forwardly therefrom. The impeller assembly 11 includes an impeller carrier 52 which is slidably mounted in the tracks 33 and is positioned between the front and rear walls 47 and 48 of the release shuttle 45. The impeller member 12 has a rear or proximal end 53 mounted in the impeller carrier 52. The impeller member 12 extends through the front wall 47 of the shuttle 45 and through the bumper wall 40 of the slide bracket 38 and terminates at a front or distal end 54. the impeller member 12 and the needle 4 are preferably formed of stainless steel].

A spring carrier 57 is slidably mounted between the lower side of the track 33 on one side of the slide housing 25 and a ledge 43 therebelow (FIG. 10). A front end 59 (FIG. 11) of the spring carrier 57 has a latch pawl 58 formed thereon which is adapted and positioned to engage the latch shoulder 42 of the slide bracket 38. The impeller extender spring 19 has one end connected to an intermediate position of the spring carrier 57 and an opposite end connected to an extender spring anchor 60 which is positioned at the rear end 31 of the slide housing 25. The impeller bias spring 22 has a rear end connected to a rear end 61 of the spring carrier 57 and a front end connected to an impeller extender cable 64.

The opposite end of the extender cable 64 is connected to the impeller carrier 52 and passes about the front wall 47 of the shuttle 45. An impeller retractor cable 66 has one end connected to the slide housing 25 at 67 (FIG. 7), has the opposite end connected to the impeller carrier 52, and passes about the rear wall 48 of the shuttle 45. The cables 64 and 66 may, in fact, be a single cable with knots separating extender and retractor sections. The term "cable" is used to describe the members 64 and 66; however, they are preferably very flexible and may be formed as a type of string, twine, or the like from a material such as nylon or the like.

Referring particularly to FIGS. 5, 13, and 17, the trigger assembly 9 includes an external trigger shell 70 and a movable trigger finger plate 72 having a plurality of movable trigger fingers 73 formed thereon. A fixed trigger finger plate 75 is positioned within the grip housing 8 and has a plurality of fixed trigger fingers 76 formed thereon. The trigger shell 70 and movable plate 72 are pivotally mounted on a trigger pivot bearing 78 formed within the housing 7.

The fingers 73 and 76 are positioned for intermeshing engagement about a trigger cable 80 upon pivoting the trigger assembly 9 into the grip housing. FIGS. 5 and 13 are somewhat diagrammatic in that the movable fingers 73 are shown disembodied from the movable plate 72, to illustrate their cooperation with the fixed fingers 76. The trigger cable 80 has a fixed end 81 anchored at a lower end of the fixed finger plate 75 and an opposite free end 82 connected to the front wall 47 of the shuttle 45 and passes about the fingers 73 and 76 in a serpentine path 84 which deepens with the degree of meshing of the fingers 73 and 76 as the trigger assembly 9 is pivoted into the grip housing 7.

The trigger cable 80 is preferably fairly flexible and strong and engages the fingers 73 and 76 with a low degree of friction and may have a form similar to a flat wound type of "silk and steel" type of guitar string. Some of the fingers 73 and 76 are provided with retainer tabs 86 to retain the trigger cable 80 threaded about the fingers 73 and 76 and to aid in assembly of the implanter apparatus 1. The arrangement of finger plates 72 and 75 and the fingers 73 and 76 enables a relatively large displacement of the free end 82 of the trigger cable 80 for a relatively small pivot angle of the trigger assembly 9. A large pulley would otherwise be required to achieve a comparable displacement of the free end 82 for the same angle of pivot of the trigger assembly 9.

The grip housing 8 and the trigger assembly 9 are configured in such a manner as to provide a magazine channel 88 through which the pellet magazine 15 extends (FIG. 17). The magazine 15 is indexed upwardly by reciprocation of the slide grip 18. A magazine feed rocker arm 90 is pivotally mounted within the rocker portion 26 of the housing 7 and has a cam follower peg 91 (FIG. 4) at a rear end and a magazine feed pawl 92 at a front end. The cam follower 91 rides in the linear cam track 44 formed in the connector link 39 of the slide bracket 38. The cam track 44 has a straight section 94 parallel to a longitudinal axis of the slide housing 25 at the rear of the connector link 39 and an angled section 95 which angles upward toward the front. Movement of the angled section 95 past the cam follower 91, upon rearward extension of the slide grip 18, raises the cam follower 81 and lowers the pawl 92, which slips past a magazine chamber 14.

Return movement of the slide grip 18 toward the front end 28 of the housing 7 lowers the cam follower 91 and raises the pawl 92, which engages a magazine chamber 14 and raises the magazine 15. The connector link 39 preferably has a snap member 96 which engages an edge of the housing 7 when the slide grip 18 is returned to its forward position to retain the slide grip 18 and the slide bracket 38 in the retracted position of the slide grip 18.

Referring to FIGS. 15 and 16, the illustrated magazine strip 15 of the implanter apparatus 1 has a capacity of twenty pellet doses stored in corresponding pellet chambers 14 which are connected by intervening webs 97. The chambers 14 are slightly conical shape and are arranged in a side by side parallel relation. The chambers 14 may have internal formations (not shown) to retain the pellets 2 therein. A plurality of strips 15 can be connected in end to end relation to increase the implanting capacity before the implanter 1 requires reloading. Each strip 15 has a connector clamp 98 at a top end and a cooperating connector bead 99 formed at a lower end on a terminating web 97. The top side of the connector clamp 98 is split to receive the lower web 97 and bead of another strip 15. The implanter apparatus may include a magazine drum 100 which is snapped onto a lower end of the grip housing 8. A plurality of end to end connected strips are rolled up into the drum 100 and are fed upwardly through the grip housing 8 therefrom. As the pellets 2 in an individual magazine strip 15 are exhausted, the empty strip 15 can be detached from the remaining strip 15 in the apparatus 1 and discarded. Each magazine strip 15 may be provided with a key tab 101 which matches with a corresponding key notch (not shown) in a magazine entry port (not shown) at the lower end of the grip housing 8 and a similar key notch (not shown) in a magazine exit port 102 at the top of the housing 7, to properly orient the magazine 15.

The implanter apparatus 1 is prepared for an implanting operation by extending the slide grip 18 rearwardly, loading a pellet magazine strip 15 into the grip housing 8, and indexing the first pellet chamber 14 into alignment with the needle 4 and impeller 12. The slide grip 18 must be extended rearwardly to clear the impeller member 12 and the magazine grip 41 from the path of the incoming magazine 15. Rearward movement of the slide grip 18 additionally engages the bumper wall 40 of the slide bracket 38 with the front wall 47 of the release shuttle 45 and urges it rearwardly. Rearward movement of the shuttle 45 retracts the impeller assembly 11 by way of the impeller retractor cable 66 passing about the rear wall 48 of the shuttle 45 and connecting to the slide housing 25. The arrangement of the retractor cable 66 causes the impeller assembly 11 to retract at twice the retraction rate of the shuttle 45 whereby the impeller carrier 52 begins the rearward stroke of the slide grip 18 just behind the front wall 47 of the shuttle 45 and ends up just in front of the rear wall 48 at the extreme rear point of the rearward stroke. Rearward movement of the shuttle 45 draws the free end 82 of the trigger cable 80 rearwardly whereby tension in the trigger cable 80 unmeshes the movable fingers 73 from the fixed fingers 76, causing the trigger assembly 9 to be pivoted outwardly to an armed position (FIG. 5). The rearward stroke of the slide grip 18 additionally lowers the magazine feed pawl 92.

The forward or return stroke of the slide grip 18 pushes the slide bracket 38 forward whereby the latch shoulder 42 engages and latches the latch pawl 58 of the spring carrier 57 and carries it forward, thereby tensioning the impeller extender spring 19. As the forward stroke continues, the magazine feed pawl 92 is raised, thereby indexing the magazine 15 upward to align a pellet chamber 14 between the needle 4 and the impeller member 12. At the forward end of the forward stroke, the snap member 96 of the connector link 39 snaps into the rocker housing 26. The implanter apparatus 1 is, thus, prepared for implanting a pellet dose 2 into the ear 20 of an animal 3. The ear 20 of the animal 3 is grasped, and the needle 4 is punctured through and underneath the hide of the ear 20, while attempting to avoid any large blood vessels.

The slide bracket 38 and spring carrier 57 form a latch mechanism 103 which retains an extension spring force in the extender spring 19. Release of the latch mechanism 103 by pivoting the trigger assembly 9 into the grip housing 8 toward a release position is a two stage process. As the trigger assembly 9 is pivoted into the grip housing 8, the shuttle 45 is drawn forward by tension in the trigger cable 80 thereby engaging the rear wall 48 of the shuttle 45 with the impeller carrier 52. The tip 54 of the impeller member 12 is pushed forward through the aligned pellet chamber 14 which urges the stack of pellets 2 just into the needle 4.

As inward pivoting of the trigger assembly 9 continues, the latch release cam 49 on the release shuttle 45 engages the latch pawl 58 and releases it from the latch shoulder 42. The spring carrier 57 snaps rearwardly under the resilient tension of the impeller extender spring 19, thereby driving the impeller member 12 forward through the impeller extender cable 64 and the impeller bias spring 22. The bias spring 22, to some extent, softens the shock of the extender spring 19 on the impeller assembly 11 and simultaneously applies a forward resilient bias on the impeller member 12, urging to a position extending entirely through the needle 4. As the needle 4 is withdrawn from the ear 20, the impeller member 12 completely ejects the pellets 2 from the needle 4 as the tip 54 of the impeller 12 emerges from the end of the needle 4, whereby the pellets 2 are left within the ear 20 of the animal 3.

In actual operation, the trigger release procedure can be carried out very quickly after inserting the needle 4 into the animal's ear 20. The spring force of the extender spring 19 does most of the work of driving the pellets 2 through the needle 4, whereby fatigue is reduced and whereby the operator can more easily concentrate on controlling the animal 3 and proper placement of the needle 4.

It is to be understood that while certain forms of the present invention have been illustrated and described herein, it is not to be limited to the specific forms or arrangement of parts described and shown.

What is claimed and desired to be secured by Letters Patent is as follows:

1. In an implanter apparatus for implanting a pellet in an animal through a needle by movement of an elongated impeller from a retracted position within an implanter housing to an extended position through said needle by pivoting a trigger from an armed position to a release position, the improvement comprising:

(a) a slide member slidably mounted on said housing, engaged with said trigger and said impeller, and operative to retract said impeller to said retracted position and extend said trigger to said armed position upon manual reciprocation of said slide member.

2. In an implanter apparatus for subcutaneously implanting a pellet in an animal through a needle by movement of an elongated impeller from a retracted position within an implanter housing to an extended position through said needle upon pivoting a trigger from an armed position to a release position, the improvement comprising:

(a) an impeller spring operatively engaged between said impeller and said housing and operable to resiliently urge said impeller toward said extended position when a spring force stored in said spring is released;

(b) a latch mechanism positioned within said housing to releasably retain a spring force in said spring;

(c) a slide mechanism slidably mounted on said housing and engaged with said trigger and said impeller in such a manner as to position said trigger in said armed position and said impeller in said retracted position and to store a spring force in said spring upon manual reciprocation of said slide mechanism; and (d) a release member connected to said trigger and operative upon movement of said trigger toward said release position to urge said impeller toward said extended position thereby releasing said impeller from said latch mechanism to enable said spring to resiliently urge said impeller toward said extended position.

3. An implanter apparatus for subcutaneously implanting a pellet in an animal and comprising:

(a) an implanter housing having a front end and a rear end;

(b) a manual grip extending from said housing;

(c) a tubular needle mounted on said front end of said housing and having a sharpened end for puncturing skin of an animal to enable implanting a pellet therethrough;

(d) a pellet magazine holding a plurality of pellets sized to be implanted through said needle and positioned relative to said housing to selectively align a pellet with said needle;

(e) an elongated impeller mounted in said housing to enable reciprocating movement between an extended position through said needle and a retracted position within said housing, said impeller being aligned with said needle to enable travel of a distal end of said impeller through said magazine to urge an aligned pellet through said needle;

(f) an impeller spring operatively engaged between said impeller and said housing and operable to resiliently urge said impeller toward said extended position when a spring force stored in said spring is released;

(g) a latch mechanism positioned within said housing to releasably retain a spring force in said spring;

(h) a trigger pivotally connected to said housing to enable movement between an extended armed position and a release position toward said grip;

(i) a slide mechanism slidably mounted on said rear end of said housing and engaged with said trigger and said impeller in such a manner as to extend said trigger to said armed position, to move said impeller to said retracted position, and to store a spring force in said spring upon manual reciprocation of said slide mechanism; and (j) a release mechanism operatively connected between said trigger and said latch mechanism and operative upon movement of said trigger toward said release position to urge said impeller toward said extended position past said latch mechanism to thereby release said impeller spring and enable said impeller spring to urge said impeller toward said extended position.

4. In an implanter apparatus for implanting a pellet in an animal through a needle by movement of an elongated impeller from a retracted position within an implanter housing to an extended position through said needle by pivoting a trigger from an armed position to a release position, the improvement comprising:

(a) a slide member slidably mounted on said housing, engaged with said trigger and said impeller, and operative to retract said impeller to said retracted position and extend said trigger to said armed position upon manual reciprocation of said slide member; and (b) a trigger cable operatively engaged between said trigger and said impeller and advancing said impeller from said retracted position toward said extended position upon pivoting said trigger.

5. An implanter apparatus as set forth in claim 4 and including:

(a) a manual grip extending from said housing; and (b) said trigger being pivotally connected to said housing and being positioned to pivot out of said grip toward said armed position and into said grip toward said release position.

6. An implanter apparatus as set forth in claim 5 and including:

(a) a pellet magazine having a plurality of pellet doses packaged therein, said magazine extending through said grip to enable said pellet doses to be successively aligned between said impeller and said needle.

7. An implanter apparatus as set forth in claim 6 and including:

(a) a magazine feed mechanism engaged between said slide member and said magazine, said feed mechanism advancing said magazine to align a successive pellet dose between said impeller and said needle each time said slide member is reciprocated.

8. An implanter apparatus as set forth in claim 4 and including:

(a) an impeller spring operatively engaged between said housing and said impeller and resiliently urging said impeller toward said extended position when a spring force in said impeller spring is released;

(b) a latch mechanism positioned within said housing to releasably retain a spring force in said impeller spring;

(c) said slide mechanism, upon reciprocation, storing a spring force in said impeller spring and setting said latch mechanism to releasably retain said spring force; and (d) said trigger, upon pivoting toward said release position, causing said latch mechanism to release said spring force to thereby urge said impeller toward said extended position.

9. An implanter apparatus as set forth in claim 4 and including:

(a) an impeller bias spring operatively engaged between said housing and said impeller and resiliently urging said impeller in a direction toward said extended position when said impeller is in said extended position.

10. In an implanter apparatus for implanting a pellet in an animal through a needle by movement of an elongated impeller from a retracted position within an implanter housing to an extended position through said needle by pivoting a trigger from an armed position to a release position, the improvement comprising:

(a) a slide member slidably mounted on said housing, engaged with said trigger and said impeller, and operative to retract said impeller to said retracted position and extend said trigger to said armed position upon manual reciprocation of said slide member; and (b) a retractor cable operatively engaged between said slide member and said impeller and urging said impeller toward said retracted position upon reciprocation of said slide member.

11. In an implanter apparatus for subcutaneously implanting a pellet in an animal through a needle by movement of an elongated impeller from a retracted position within an implanter housing to an extended position through said needle upon pivoting a trigger from an armed position to a release position, the improvement comprising:

(a) an impeller spring operatively engaged between said impeller and said housing and operable to resiliently urge said impeller toward said extended position when a spring force stored in said spring is released;

(b) a latch mechanism positioned within said housing to releasably retain a spring force in said spring;

(c) a slide mechanism slidably mounted on said housing and engaged with said trigger and said impeller in such a manner as to position said trigger in said armed position and said impeller in said retracted position and to store a spring force in said spring upon manual reciprocation of said slide mechanism; and (d) a release member connected to said trigger and operative upon movement of said trigger toward said release position to urge said impeller toward said extended position thereby releasing said impeller from said latch mechanism to enable said spring to resiliently urge said impeller toward said extended position, said release member including a trigger cable operatively engaged between said trigger and said impeller and advancing said impeller from said retracted position toward said extended position upon pivoting said trigger.

12. An implanter apparatus as set forth in claim 11 and including:

(a) a manual grip extending from said housing; and (b) said trigger being pivotally connected to said housing and being positioned to pivot out of said grip toward said armed position and into said grip toward said release position.

13. An implanter apparatus as set forth in claim 12 and including:

(a) a pellet magazine having a plurality of pellet doses packaged therein, said magazine extending through said grip to enable said pellet doses to be successively aligned between said impeller and said needle.

14. An implanter apparatus as set forth in claim 13 and including:

(a) a magazine feed mechanism engaged between said slide member and said magazine, said feed mechanism advancing said magazine to align a successive pellet dose between said impeller and said needle each time said slide member is reciprocated.

15. An implanter apparatus as set forth in claim 14 wherein said magazine feed mechanism includes:

(a) a rocker arm pivotally mounted on said housing, having a magazine pawl at a front end and a cam follower at an opposite rear end; and (b) said slide mechanism including a linear cam having said cam follower engaged therewith in such a manner that reciprocation of said slide mechanism causes said magazine pawl to successively advance said magazine.

16. An implanter apparatus as set forth in claim 11 and including:

(a) an impeller bias spring operatively engaged between said housing and said impeller and resiliently urging said impeller in a direction toward said extended position when said impeller is in said extended position.

17. In an implanter apparatus for subcutaneously implanting a pellet in an animal through a needle by movement of an elongated impeller from a retracted position within an implanter housing to an extended position through said needle upon pivoting a trigger from an armed position to a release position, the improvement comprising:

(a) an impeller spring operatively engaged between said impeller and said housing and operable to resiliently urge said impeller toward said extended position when a spring force stored in said spring is released;

(b) a latch mechanism positioned within said housing to releasably retain a spring force in said spring;

(c) a slide mechanism slidably mounted on said housing and engaged with said trigger and said impeller in such a manner as to position said trigger in said armed position and said impeller in said retracted position and to store a spring force in said spring upon manual reciprocation of said slide mechanism;

(d) a release member connected to said trigger and operative upon movement of said trigger toward said release position to urge said impeller toward said extended position thereby releasing said impeller from said latch mechanism to enable said spring to resiliently urge said impeller toward said extended position; and (e) a retractor cable operatively engaged between said slide member and said impeller and urging said impeller toward said retracted position upon reciprocation of said slide member.

18. In an implanter apparatus for subcutaneously implanting a pellet in an animal through a needle by movement of an elongated impeller from a retracted position within an implanter housing to an extended position through said needle upon pivoting a trigger from an armed position to a release position, the improvement comprising:

(a) an impeller spring operatively engaged between said impeller and said housing and operable to resiliently urge said impeller toward said extended position when a spring force stored in said spring is released;

(b) a latch mechanism positioned within said housing to releasably retain a spring force in said spring;

(c) a slide mechanism slidably mounted on said housing and engaged with said trigger and said impeller in such a manner as to position said trigger in said armed position and said impeller in said retracted position and to store a spring force in said spring upon manual reciprocation of said slide mechanism;

(d) a release member connected to said trigger and operative upon movement of said trigger toward said release position to urge said impeller toward said extended position thereby releasing said impeller from said latch mechanism to enable said spring to resiliently urge said impeller toward said extended position;

(e) said housing having a front needle end with said needle mounted thereon and an opposite back end;

(f) an elongated release shuttle slidably mounted within said housing, said shuttle having a front end longitudinally spaced from a rear end and having a release cam positioned at said front end;

(g) an impeller carrier slidably mounted within said housing between said front end and said rear end of said shuttle, said impeller having a proximal end connected to said carrier and extending through said front end of said shuttle;

(h) an impeller retractor cable connected between said housing and said impeller carrier and passing about said rear end of said shuttle in such a manner that rearward movement of said shuttle toward said back end of said housing causes rearward movement of said impeller carrier;

(i) said latch mechanism including a spring carrier slidably mounted within said housing and having a latch pawl positioned at a front pawl end of said spring carrier, said spring carrier having a rear anchor end opposite said pawl end;

(j) said impeller spring being connected between said housing and said spring carrier and resiliently urging said spring carrier rearward;

(k) an impeller extender cable connected between said impeller carrier and said spring carrier and passing about said front end of said shuttle in such a manner that rearward movement of said spring carrier when said shuttle is in a forward position causes forward movement of said impeller carrier;

(l) said slide mechanism including an internal slide bracket slidably mounted within said housing, including a shuttle retractor positioned forward of said front end of said shuttle, having said impeller extending therethrough, and having a latch shoulder positioned in such a manner that rearward movement of said slide bracket urges said shuttle rearward to a position at which said spring carrier pawl engages said latch shoulder and forward movement of said slide bracket urges said spring carrier forward thereby storing a spring force in said impeller spring; and (m) a trigger cable connected between said shuttle and said trigger in such a manner that rearward movement of said shuttle pivots said trigger toward said armed position and movement of said trigger toward said release position draws said shuttle and said impeller carrier forward to a position at which said release cam engages and releases said pawl from said latch shoulder thereby releasing said spring carrier to move rearwardly and resiliently urging said impeller toward said extended position by way of said extender cable.

19. An implanter apparatus as set forth in claim 18 and including:

(a) an impeller bias spring connecting said extender cable to said spring carrier and resiliently urging said impeller in a direction toward said extended position when said impeller is in said extended position.

20. An implanter apparatus for subcutaneously implanting a pellet in an animal and comprising:

(a) an implanter housing having a front end and a rear end;

(b) a manual grip extending from said housing;

(c) a tubular needle mounted on said front end of said housing and having a sharpened end for puncturing skin of an animal to enable implanting a pellet therethrough;

(d) a pellet magazine holding a plurality of pellets sized to be implanted through said needle and positioned relative to said housing to selectively align a pellet with said needle;

(e) an elongated impeller mounted in said housing to enable reciprocating movement between an extended position through said needle and a retracted position within said housing, said impeller being aligned with said needle to enable travel of a distal end of said impeller through said magazine to urge an aligned pellet through said needle;

(f) an impeller spring operatively engaged between said impeller and said housing and operable to resiliently urge said impeller toward said extended position when a spring force stored in said spring is released;

(g) a latch mechanism positioned within said housing to releasably retain a spring force in said spring;

(h) a trigger pivotally connected to said housing to enable movement between an extended armed position and a release position toward said grip;

(i) a slide mechanism slidably mounted on said rear end of said housing and engaged with said trigger and said impeller in such a manner as to extend said trigger to said armed position, to move said impeller to said retracted position, and to store a spring force in said spring upon manual reciprocation of said slide mechanism;

(j) a release mechanism operatively connected between said trigger and said latch mechanism and operative upon movement of said trigger toward said release position to urge said impeller toward said extended position past said latch mechanism to thereby release said impeller spring and enable said impeller spring to urge said impeller toward said extended position; and (k) a trigger cable operatively engaged between said trigger and said impeller and advancing said impeller from said retracted position toward said extended position upon pivoting said trigger.

21. An implanter apparatus as set forth in claim 20 and including:

(a) said pellet magazine extending through said grip.

22. An implanter apparatus as set forth in claim 20 and including:

(a) a magazine feed mechanism engaged between said slide member and said magazine, said feed mechanism advancing said magazine to align a successive pellet dose between said impeller and said needle each time said slide member is reciprocated.

23. An implanter apparatus as set forth in claim 22 wherein said magazine feed mechanism includes:

(a) a rocker arm pivotally mounted on said housing, having a magazine pawl at a front end and a cam follower at an opposite rear end; and (b) said slide mechanism including a linear cam having said cam follower engaged therewith in such a manner that reciprocation of said slide mechanism causes said magazine pawl to successively advance said magazine.

24. An implanter apparatus as set forth in claim 20 and including:

(a) an impeller bias spring operatively engaged between said housing and said impeller and resiliently urging said impeller in a direction toward said extended position when said impeller is in said extended position.

25. An implanter apparatus for subcutaneously implanting a pellet in an animal and comprising:

(a) an implanter housing having a front end and a rear end;

(b) a manual grip extending from said housing;

(c) a tubular needle mounted on said front end of said housing and having a sharpened end for puncturing skin of an animal to enable implanting a pellet therethrough;

(d) a pellet magazine holding a plurality of pellets sized to be implanted through said needle and positioned relative to said housing to selectively align a pellet with said needle;

(e) an elongated impeller mounted in said housing to enable reciprocating movement between an extended position through said needle and a retracted position within said housing, said impeller being aligned with said needle to enable travel of a distal end of said impeller through said magazine to urge an aligned pellet through said needle;

(f) an impeller spring operatively engaged between said impeller and said housing and operable to resiliently urge said impeller toward said extended position when a spring force stored in said spring is released;

(g) a latch mechanism positioned within said housing to releasably retain a spring force in said spring;

(h) a trigger pivotally connected to said housing to enable movement between an extended armed position and a release position toward said grip;

(i) a slide mechanism slidably mounted on said rear end of said housing and engaged with said trigger and said impeller in such a manner as to extend said trigger to said armed position, to move said impeller to said retracted position, and to store a spring force in said spring upon manual reciprocation of said slide mechanism;

(j) a release mechanism operatively connected between said trigger and said latch mechanism and operative upon movement of said trigger toward said release position to urge said impeller toward said extended position past said latch mechanism to thereby release said impeller spring and enable said impeller spring to urge said impeller toward said extended position; and (k) a retractor cable operatively engaged between said slide member and said impeller and urging said impeller toward said retracted position upon reciprocation of said slide member.

26. An implanter apparatus for subcutaneously implanting a pellet in an animal and comprising:

(a) an implanter housing having a front end and a rear end;

(b) a manual grip extending from said housing;

(c) a tubular needle mounted on said front end of said housing and having a sharpened end for puncturing skin of an animal to enable implanting a pellet therethrough;

(d) a pellet magazine holding a plurality of pellets sized to be implanted through said needle and positioned relative to said housing to selectively align a pellet with said needle;

(e) an elongated impeller mounted in said housing to enable reciprocating movement between an extended position through said needle and a retracted position within said housing, said impeller being aligned with said needle to enable travel of a distal end of said impeller through said magazine to urge an aligned pellet through said needle;

(f) an impeller spring operatively engaged between said impeller and said housing and operable to resiliently urge said impeller toward said extended position when a spring force stored in said spring is released;

(g) a latch mechanism positioned within said housing to releasably retain a spring force in said spring;

(h) a trigger pivotally connected to said housing to enable movement between an extended armed position and a release position toward said grip;

(i) a slide mechanism slidably mounted on said rear end of said housing and engaged with said trigger and said impeller in such a manner as to extend said trigger to said armed position, to move said impeller to said retracted position, and to store a spring force in said spring upon manual reciprocation of said slide mechanism;

(j) a release mechanism operatively connected between said trigger and said latch mechanism and operative upon movement of said trigger toward said release position to urge said impeller toward said extended position past said latch mechanism to thereby release said impeller spring and enable said impeller spring to urge said impeller toward said extended position;

(k) an elongated release shuttle slidably mounted within said housing, said shuttle having a front end longitudinally spaced from a rear end and having a release cam positioned at said front end;

(l) an impeller carrier slidably mounted within said housing between said front end and said rear end of said shuttle, said impeller having a proximal end connected to said carrier and extending through said front end of said shuttle;

(m) an impeller retractor cable connected between said housing and said impeller carrier and passing about said rear end of said shuttle in such a manner that rearward movement of said shuttle toward said back end of said housing causes rearward movement of said impeller carrier;

(n) said latch mechanism including a spring carrier slidably mounted within said housing and having a latch pawl positioned at a front pawl end of said spring carrier, said spring carrier having a rear anchor end opposite said pawl end;

(o) said impeller spring being connected between said housing and said spring carrier and resiliently urging said spring carrier rearward;

(p) an impeller extender cable connected between said impeller carrier and said spring carrier and passing about said front end of said shuttle in such a manner that rearward movement of said spring carrier when said shuttle is in a forward position causes forward movement of said impeller carrier;

(q) said slide mechanism including an internal slide bracket slidably mounted within said housing, including a shuttle retractor positioned forward of said front end of said shuttle, having said impeller extending therethrough, and having a latch shoulder positioned in such a manner that rearward movement of said slide bracket urges said shuttle rearward to a position at which said spring carrier pawl engages said latch shoulder and forward movement of said slide bracket urges said spring carrier forward thereby storing a spring force in said impeller spring; and (r) a trigger cable connected between said shuttle and said trigger in such a manner that rearward movement of said shuttle pivots said trigger toward said armed position and movement of said trigger toward said release position draws said shuttle and said impeller carrier forward to a position at which said release cam engages and releases said pawl from said latch shoulder thereby releasing said spring carrier to move rearwardly and resiliently urging said impeller toward said extended position by way of said extender cable.

27. An implanter apparatus as set forth in claim 26 and including:

(a) an impeller bias spring connecting said extender cable to said spring carrier and resiliently urging said impeller in a direction toward said extended position when said impeller is in said extended position.

* * * * *